United States Patent [19]

Jackman

[11] Patent Number: 5,408,033

[45] Date of Patent: Apr. 18, 1995

[54] PROCESS FOR THE PREPARATION OF AN EPOXIDE FROM KETONES USING AN ALCOHOL OR ETHER CATALYST

[75] Inventor: Dennis E. Jackman, Prairie Village, Kans.

[73] Assignee: Miles Inc., Pittsburgh, Pa.

[21] Appl. No.: 41,117

[22] Filed: Apr. 1, 1993

[51] Int. Cl.$^6$ ............................................. C07D 301/02
[52] U.S. Cl. ....................................... 528/421; 549/519
[58] Field of Search .......................... 549/519; 528/421

[56] References Cited

U.S. PATENT DOCUMENTS

| | | | |
|---|---|---|---|
| 4,960,911 | 10/1990 | Zerbes et al. | 549/519 |
| 4,988,829 | 1/1991 | Fiedler et al. | 549/519 |
| 4,992,565 | 12/1991 | Mohrmann et al. | 549/519 |

OTHER PUBLICATIONS

"Organic Chemistry", Stanley H. Pine, McGraw Hill Inc. 1987.

*Primary Examiner*—Frederick Krass
*Attorney, Agent, or Firm*—Joseph C. Gil; Lyndanne M. Whalen; Godfried R. Akorli

[57] ABSTRACT

An epoxide is produced by reacting a sulfonium salt with a ketone in the presence of a low molecular weight alcohol or ether and an alkali metal hydroxide at a temperature of from about 60° to about 90° C. The alkali metal hydroxide is in the solid form. The reaction is generally carried out in the presence of an organic solvent such as toluene. The preferred low molecular weight ether is diethylene glycol. Water is not added to the reaction mixture.

16 Claims, No Drawings

PROCESS FOR THE PREPARATION OF AN EPOXIDE FROM KETONES USING AN ALCOHOL OR ETHER CATALYST

BACKGROUND OF THE INVENTION

The present invention relates to a process for the preparation of epoxides such as the known 2-(4-chlorophenylethyl)-2-tert-butyloxirane, which can be used as intermediate for the synthesis of the fungicide 1-(4-chlorophenyl)-3-(1,2,4-triazol-1-ylmethyl)-4,4-dimethylpentan-3-ol.

It is known that oxiranes can be prepared by reacting dimethyl sulfide with methyl bromide and then reacting the resulting trimethylsulfonium bromide with carbonyl compounds in the presence of an inert organic solvent and in the presence of a strong base, such as sodium hydride, sodium amide or potassium tert-butylate (See, e.g., Ber. 96, 1881–1890 (1963)).

It is also known that 2-(4-chlorophenyl-ethyl)-2-tert-butyloxirane can be synthesized by treating dimethyl sulfide with methyl bromide in the presence of an inert organic diluent and reacting the resulting trimethylsulfonium bromide with 1-(4-chlorophenyl)-4,4-dimethylpentan-3-one in the presence of a base and also in the presence of an inert organic diluent at temperatures between 0° C. and 60° C. (See, e.g., DE-OS 3,315,510). Relatively pure 2-(4-chlorophenylethyl)-2-tert-butyloxirane can be prepared by this process. However, this reaction requires relatively long reaction times and the yield is not always sufficient for practical purposes. Another disadvantage of this disclosed process is that the preparation of trimethylsulfonium bromide can only be achieved at a relatively low yield of about 75%. The space/time yields in this process only reach values of about 6 g/l h.

U.S. Pat. No. 4,988,829 discloses a process for the production of 2-(4-chlorophenylethyl)-2-tert-butyl oxirane in which a suspension of trimethylsulfonium bromide having a solids content between 10 and 70% is formed by mixing a solution of trimethylsulfonium bromide in a methanol/toluene mixture with heated toluene while distilling off a methanol/toluene mixture. This suspension of trimethylsulfonium bromide in toluene is then reacted with 2,2-dimethyl-5-p-chlorophenyl-3-pentanone in the presence of solid potassium hydroxide, diethylene glycol and water at a temperature between 20° and 120° C. The need to form a trimethylsulfonium bromide suspension and the use of water in the reaction mixture are among the disadvantages of this process.

SUMMARY OF THE INVENTION

It is an object of the present invention to provide a relatively simple process for the production of epoxides in which a suspension of a sulfonium salt need not be employed.

It is another object of the present invention to provide a process for the production of epoxides in which an organic solvent and water need not be employed.

It is also an object of the present invention to provide a relatively simple process for the production of epoxides in high yields.

These and other objects which will be apparent to those skilled in the art are accomplished by reacting a sulfonium salt with a ketone in the presence of a catalyst, a solid alkali metal hydroxide and optionally, an organic solvent and/or water. The catalysts employed in this process are molecular weight alcohols and ethers such as the particularly preferred diethylene glycol. This reaction is carried out at a temperature of from about 60° to about 90° C. The reactants are typically used in quantities such that for every mole of ketone, from 1.1 to about 1.5 moles of sulfonium salt, from 2 to 4 moles of solid alkali metal hydroxide and from about 0 to about 0.07 moles of low molecular weight alcohol or ether are present.

DETAILED DESCRIPTION OF THE PRESENT INVENTION

The present invention relates to a process for the production of epoxides. In this process, a ketone is reacted with a sulfonium salt in the presence of a solid alkali metal hydroxide at a temperature of from about 60° to about 90° C. Lower molecular weight alcohols or ethers are generally used as catalysts in this process, but it has been found that the amount of catalyst required is dependent upon the amount of organic solvent present.: The less organic solvent (e.g., toluene) present, the less catalyst required. If no organic solvent is present in the reaction mixture, no catalyst need be present. However, it is preferred that some catalyst still be included in the reaction mixture. Water is not added to the reaction mixture prior to completion of the reaction. In fact, it is preferred that no water, even in residual amounts, be present in the reaction mixture.

Any of the known ketones, particularly alkyl ketones, may be used in the process of the present invention. Examples of suitable ketones include: cyclohexanone, acetophenone, 1-alkyl-4-piperidinones, and adamantanone. 2,2-dimethyl-5-p-chlorophenyl-3-pentanone is particularly preferred.

Any of the known sulfonium salts may be used in the process of the present invention. Suitable sulfonium salts include: trimethylsulfonium bromide, trimethylsulfonium chloride, and trimethylsulfonium methylsulfate. Trimethylsulfonium bromide is particularly preferred. The sulfonium salt is generally used in a quantity such that for every mole of ketone present, from 1.1 to 1.5 moles, preferably about 1.3 moles of sulfonium salt are present.

Any of the known low molecular weight alcohols and ethers (i.e., alcohols and ethers having a molecular weight of less than 400) may be used as a catalyst in the process of the present invention. Examples of suitable catalysts include: methanol, isopropanol, t-butanol, tris-3,6-dioxaheptylamine, crown ethers glyme, diglyme, ethylene glycol, diethylene glycol, propylene glycol, and polyethylene glycol. Diethylene glycol is particularly preferred. The optimum amount of catalyst is dependent upon the volume of organic solvent employed, if any. The more solvent present in the reaction mixture, the more catalyst required. If an organic solvent is used, it is preferred that at least 1 ml of catalyst per mole of ketone, more preferably from 1 to 8 ml of catalyst per mole of ketone and most preferably about 5 ml of catalyst per mole of ketone be included in the reaction mixture. Where no organic solvent is employed, no low molecular weight alcohol or ether need be used. If a low molecular weight alcohol or ether is included in a reaction mixture in which no organic solvent is present, the low molecular weight alcohol or ether is generally used in an amount of from 0 to about 1 ml for each mole of ketone present.

Any of the known alkali metal hydroxides may be used as the base in the process of the present invention. Potassium hydroxide is particularly preferred. The hydroxide must be used in a solid form such as flakes, pellets, granules or a powder. Powdered hydroxide is particularly preferred. The hydroxide is included in the reaction mixture in a quantity such that from 2 to 4 moles of hydroxide, preferably from about 2.5 to about 3.0 moles of hydroxide, most preferably about 2.8 moles of hydroxide are present for every mole of ketone.

Any of the known hydrocarbon organic solvents may be used in the practice of the process of the present invention. Suitable solvents include: toluene, benzene, xylene, methylcyclohexane and chlorobenzene. Toluene is particularly preferred. It is possible to carry out the process of the present invention in the absence of solvent. However, it is preferred that a solvent be used in a quantity such that from about 100 to about 500 ml, most preferably about 250 ml of solvent are present for every mole of ketone included in the reaction mixture.

In a preferred embodiment of the present invention, from about 1.1 to about 1.5 moles of sulfonium salt, from about 2 to about 4 moles of alkali metal hydroxide and from about 0.01 to about 0.07 moles of low molecular weight alcohol or ether are present in the reaction mixture for each mole of ketone. In a particularly preferred embodiment of the invention, about 5 ml of diethylene glycol, about 2.8 moles of potassium hydroxide and about 1.3 moles of trimethylsulfonium bromide are present in the reaction mixture for each mole of ketone.

The process of the present invention may be carried out at a temperature of from about 60° to about 90° C., preferably about 80° C. The reactants may be combined in any order at any temperature, but it is preferred that all of the reactants be combined at ambient temperature and then heated to 60°–90° C. In another preferred embodiment, about 20% of the ketone is initially combined with the other reactants, the mixture is heated to 60°–90° C., and the remaining ketone is added in increments over a period of from 1–2 hours.

It is possible to prepare epoxides by the process of the present invention in a short period of time and in a significantly higher yield than by the known process in which trimethylsulfonium bromide serves as generator of methylene.

The process of the present invention is characterized by several advantages. The required reaction components are available on an industrial scale and easy to handle. Since the reaction proceeds very quickly under the conditions according to the invention, space/time yields of 50 to 60 g/h are obtained. Another advantage is that the workup of the resulting reaction mixture does not present any difficulties and the product epoxide is obtained in extremely high yield (i.e., greater than 98%) and excellent purity.

The process of the present Invention can be carried out either under inert gas atmosphere or in the absence of any special inert gas atmosphere.

The workup of the reaction mixture to recover the product epoxide is in general carried out by adding water to the reaction mixture, separating the aqueous phase, washing the remaining organic phase with water and then optionally after previous filtration, concentrating the organic phase first at atmospheric pressure and then under reduced pressure by distilling off the volatile components. The solvent can also be removed by steam distillation.

The 2-(4-chlorophenylethyl)-2-tert.-butyloxirane which may be prepared by the process according to the invention is a useful intermediate for the synthesis of 1-(4-chlorophenyl)-3-(1,2,4-triazol-1-ylmethyl)-4,4-dimethylpentan-3-one, which has excellent plant growth regulating and fungicidal properties (See, e.g., EP-A- 0,040,345).

Having thus described my invention, the following Examples are given as being illustrative thereof. All parts and percentages given in these Examples are parts by weight and percentages by weight unless otherwise indicated.

EXAMPLES

Example 1

68.7 grams (0.3 mole) of 2,2-dimethyl-5-p-chlorophenyl-3-pentanone, 61.2 grams (0.3g mole) trimethylsulfonium bromide, 2.5 ml diethylene glycol, 120 ml toluene and 56 grams (0.9 g mole) of potassium hydroxide were charged to a 500 ml flask in the order named. The contents of the flask were stirred and heated to 80° C. for 8 hours. 120 ml of water were then added to separate the mixture into two phases. The organic phase was isolated and then steam distilled to remove any solvent. 74.6 grams of the oily epoxide were recovered. The recovered product had a purity of 94.9%. The net yield of epoxide was 98.9%.

Example 2

120 ml of water saturated toluene, 1 ml water, 61.2 grams trimethylsulfonium bromide, 2.5 ml of diethylene glycol, 13 grams of 2,2-dimethyl-5-p-chlorophenyl-3-pentanone and 56.1 grams of potassium hydroxide in flake form were charged to a 500 ml flask. The contents of the flask were heated with stirring to 80° C. and 55 grams of additional 2,2-dimethyl-5-p-chlorophenyl-3-pentanone were added dropwise over a period of 1.5 hours. After about 8 hours, only about 1% unreacted ketone remained. The yield of epoxide was 92.9%.

This example illustrates that small amounts of water in the reaction mixture do not prevent the desired reaction from proceeding. However, the inclusion of water in even small amounts does result in a reduction of epoxide yield.

Example 3

68.7 grams of 2,2-dimethyl-5-p-chlorophenyl-3-pentanone, 61.2 grams trimethylsulfonium bromide, 3 ml diethylene glycol, and 120 ml toluene were charged to a 500 ml flask. The contents of the flask were heated to 90° C., cooled to 80° C. and then 56 grams of potassium hydroxide were added all at once. Only a 1.5° C. exotherm was measured. The reaction proceeded normally.

This example illustrates that the process of the present invention may be safely carried out without including water in the reaction mixture.

Example 4

220 grams (0.96 mole) 2,2-dimethyl-5-p-chlorophenyl-3-pentanone, 223 grams (1.42 mole) trimethylsulfonium bromide and 181 grams (2.91 mole) of potassium hydroxide in flake form were charged to a 500 ml flask. The contents of the flask were heated with stirring to 80° C., while dimethylsulfide was distilled out. After 3.5 hours, 98% of product epoxide had formed. After 4.5 hours the yield of product epoxide was 99.1%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is

1. A process comprising reacting a sulfonium salt with a ketone in the presence of about 0.01 to about 0.07 moles, per mole of ketone, an alcohol having a molecular weight of less than 400 or an ether having a molecular weight of less than 400, and selected from the group consisting of methanol, isopropanol, t-butanol, tris-3,6-dioxaheptylamine, crown ethers, glyme, diglyme, ethylene glycol, diethylene glycol, propylene glycol and polyethylene glycol, and an alkali metal hydroxide in solid form at a temperature of from about 60° to about 90° C. in which no water is added prior to completion of the reaction, said reaction being conducted so that a monoepoxide is obtained.

2. The process of claim 1 in which the sulfonium salt is a trimethylsulfonium salt.

3. The process of claim 1 in which the sulfonium salt is trimethylsulfonium bromide.

4. The process of claim 1 in which the ketone is 2,2-dimethyl-5-p-chlorophenyl-3-pentanone.

5. The process of claim 1 in which the alcohol or ether is selected from the group consisting of isopropanol, t-butanol, tris-3,6-dioxaheptylamine, crown ethers, glyme, diglyme, ethylene glycol and propylene glycol.

6. The process of claim 1 wherein the ether is diethylene glycol.

7. The process of claim 1 in which the alkali metal hydroxide is potassium hydroxide.

8. The process of claim 1 in which no organic solvent selected from the group consisting of toluene, benzene, xylene, methylcyclohexane and chlorobenzene is included in the reaction mixture.

9. The process of claim 1 in which an organic solvent is included in the reaction mixture.

10. The process of claim 1 in which toluene is included in the reaction mixture.

11. The process of claim 10 wherein diethylene glycol is present as the ether in an amount of from 1 to 8 ml for each mole of ketone present.

12. The process of claim 8 wherein diethylene glycol is present as the ether.

13. The process of claim 1 in which for every mole of ketone, from about 1.1 to about 1.5 moles of sulfonium salt, from about 2 to about 4 moles of alkali metal hydroxide and from about 0.01 to about 0.07 moles of alcohol or ether are present.

14. The process of claim 1 in which for every mole of ketone, about 5 ml diethylene glycol, about 2.8 moles potassium hydroxide, and about 1.3 moles trimethylsulfonium bromide are present.

15. The process of claim 14 in which from 100 to 500 ml toluene are included in the reaction mixture.

16. The process of claim 14 in which the ketone is 2,2-dimethyl-5-p-chlorophenyl-3-pentanone.

* * * * *